United States Patent [19]

Rougee et al.

[11] Patent Number: 5,699,446

[45] Date of Patent: Dec. 16, 1997

[54] METHOD FOR THE ACQUISITION OF IMAGES OF A BODY BY THE ROTATIONAL POSITIONING OF A RADIOLOGY DEVICE, NOTABLY AN ANGIOGRAPHY DEVICE

[75] Inventors: Anne Rougee, Palaiseau; Michel Hommerin, Paris; Jean Lienard, Clamart, all of France

[73] Assignee: GE Medical Systems S.A., Buc, France

[21] Appl. No.: 245,140

[22] Filed: May 17, 1994

[30] Foreign Application Priority Data

May 13, 1993 [FR] France ................. 93 05778

[51] Int. Cl.$^6$ ................................................ G06K 9/00
[52] U.S. Cl. ................................ 382/130; 382/132
[58] Field of Search .................... 364/413.13, 413.14, 364/413.15, 413.16, 413.23, 413.22, 413.19; 378/4, 21, 197.193, 195, 196; 382/131, 291, 130, 285, 154, 103, 128, 132, 153, 293, 312, 317, 318, 319; 356/2, 3, 3.07

[56] References Cited

U.S. PATENT DOCUMENTS

| | | | |
|---|---|---|---|
| 3,710,106 | 1/1973 | Loucheur et al. | 250/66 |
| 3,743,200 | 7/1973 | Hommerin | 242/67 |
| 3,775,613 | 11/1973 | Hommerin | 250/525 |
| 3,849,660 | 11/1974 | Hommerin | 250/570 |
| 3,879,030 | 4/1975 | Hommerin | 271/8 |
| 4,646,148 | 2/1987 | Lienard et al. | 358/135 |
| 4,739,308 | 4/1988 | Lienard | 340/347 DD |
| 4,875,165 | 10/1989 | Fencil et al. | 364/413.22 |
| 4,916,544 | 4/1990 | Lienard et al. | 358/262.1 |
| 4,984,160 | 1/1991 | Saint Felix et al. | 364/413.19 |
| 5,029,336 | 7/1991 | Micheron et al. | 378/4 |
| 5,038,371 | 8/1991 | Janssen et al. | 378/4 |
| 5,048,103 | 9/1991 | Leclerc et al. | 382/44 |
| 5,121,419 | 6/1992 | Micheron et al. | 378/4 |
| 5,123,037 | 6/1992 | Picard et al. | 378/99 |
| 5,175,773 | 12/1992 | Garreau et al. | 364/413.16 |
| 5,218,534 | 6/1993 | Trousset et al. | 364/413.17 |
| 5,241,471 | 8/1993 | Trousset et al. | 364/413.19 |
| 5,287,274 | 2/1994 | Saint Felix et al. | 364/413.15 |

FOREIGN PATENT DOCUMENTS

| | | | |
|---|---|---|---|
| 0333256 A1 | 9/1989 | European Pat. Off. | A61B 6/00 |
| 2656211 A1 | 12/1989 | France | A61B 6/02 |
| 2086700 | 5/1982 | United Kingdom | G03B 41/16 |

OTHER PUBLICATIONS

Joseph Sitomer et al.; "Computer Image–Guided Gantry Positioning"; pp. 1–16; Department of Internal Medicine, Division of Cardiology, University of Michigan. (No Date) (No Publisher).

Primary Examiner—Leo Boudreau
Assistant Examiner—Bijan Tadayon
Attorney, Agent, or Firm—Nilles & Nilles, S.C.

[57] ABSTRACT

To acquire the images around an elongated object, the direction of this object is identified. To this end, in a first image, a point constituting an image of a locus of the object is designated and localized. The image of the epipolar straight line that connects the focal spot of the X-ray tube to the localized point is plotted in the second image. In this image of the epipolar straight line, a point homologous to the point in the first image is designated and localized. From the localizations of these points, the position in space of the characteristic point is deduced. This operation is reiterated for a second characteristic locus. The orientation of the object is deduced from these two characteristic loci. The position of the imaging device is then set accordingly.

15 Claims, 4 Drawing Sheets

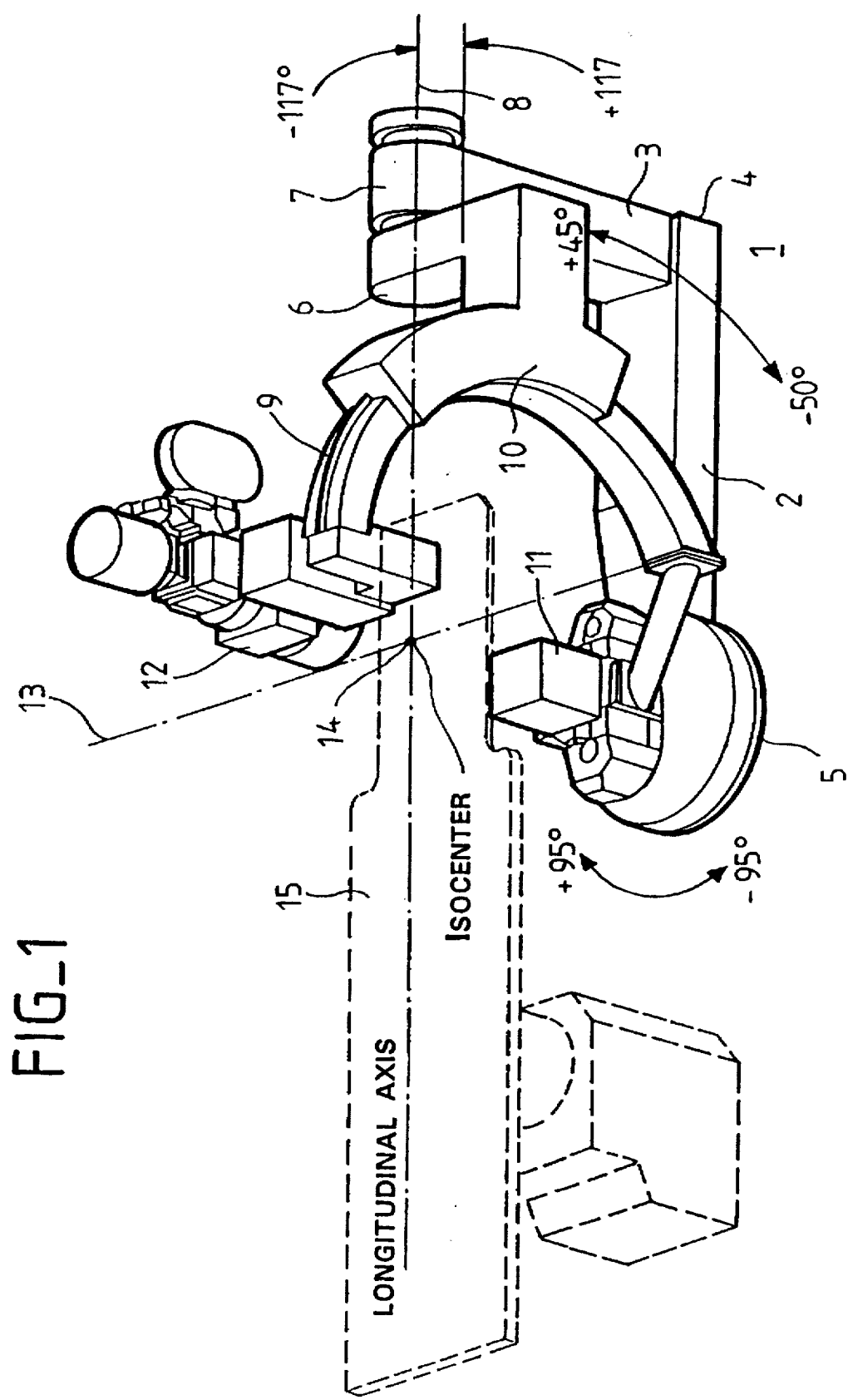
FIG_1

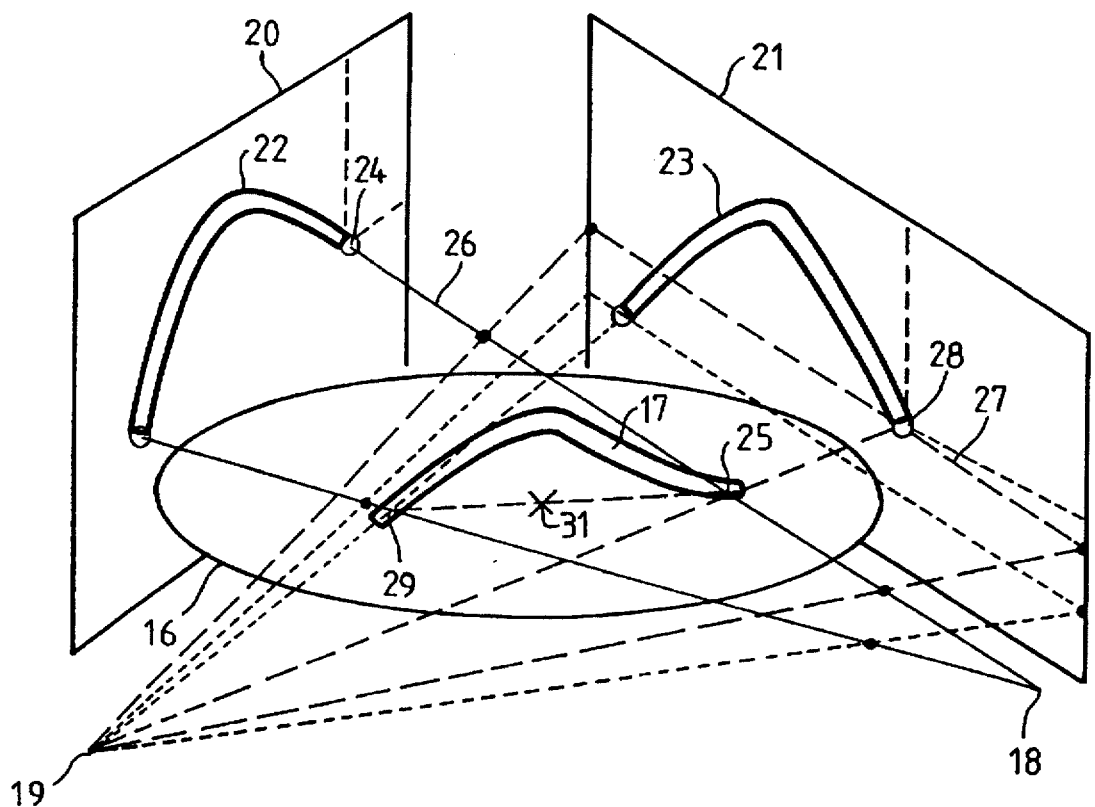
FIG_2
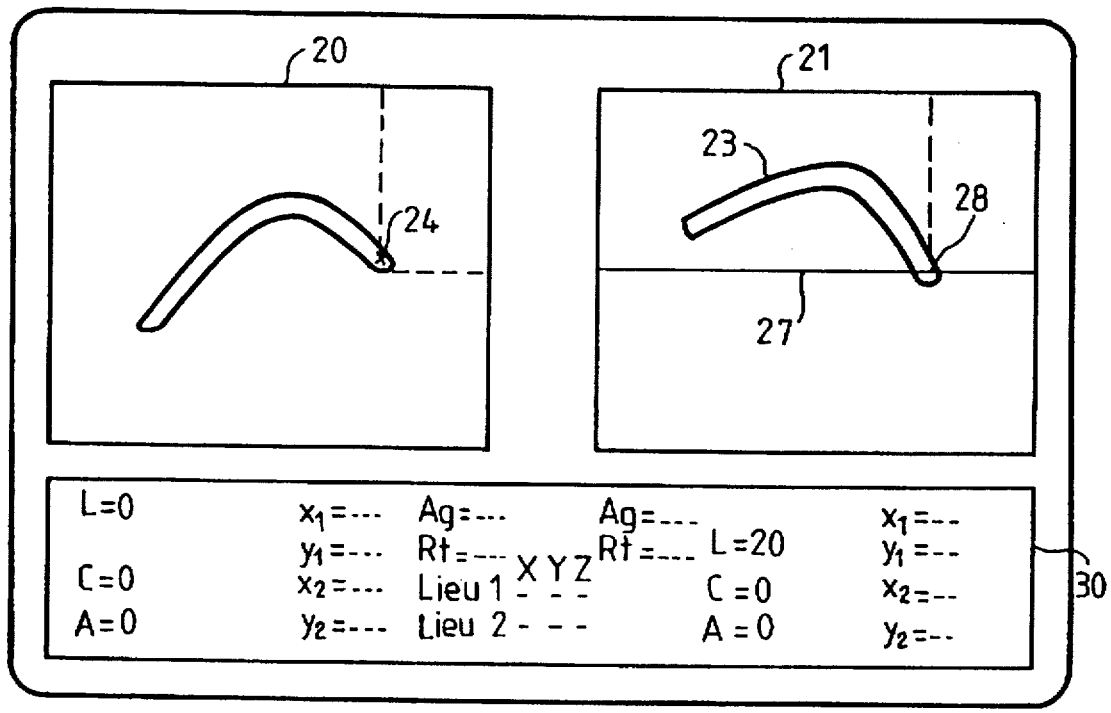
FIG_3

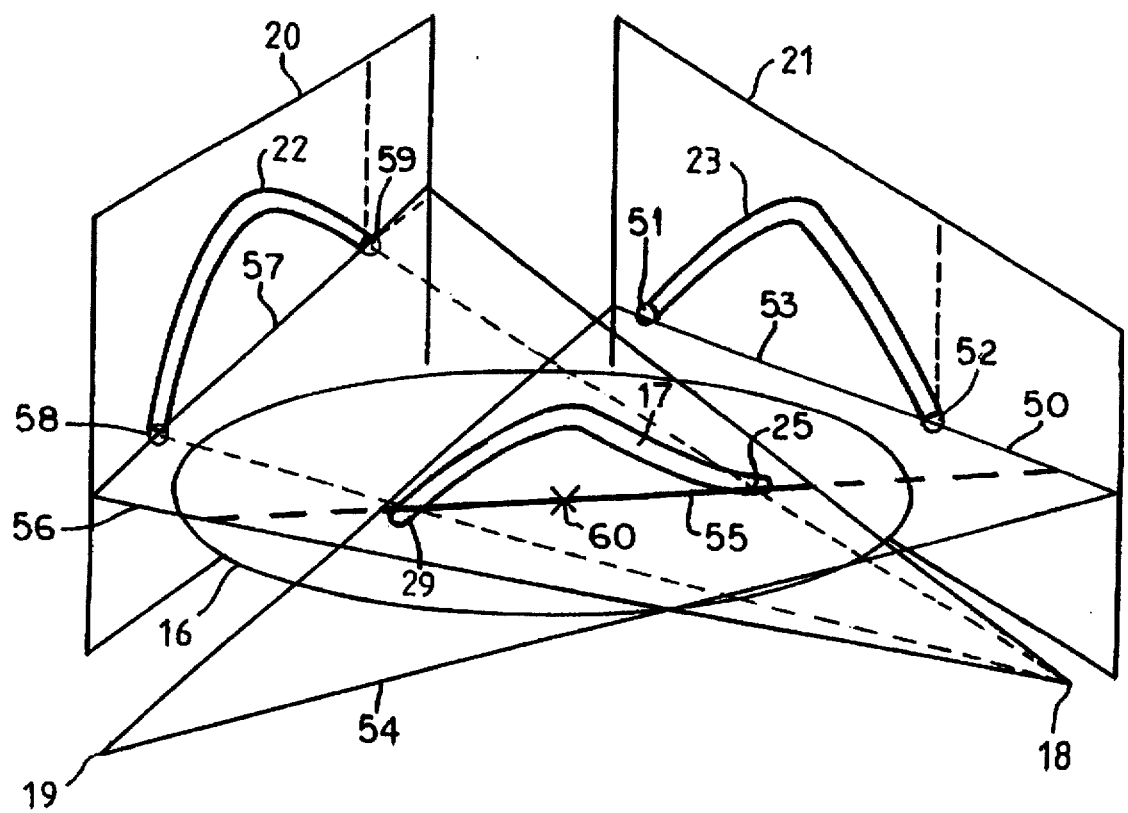
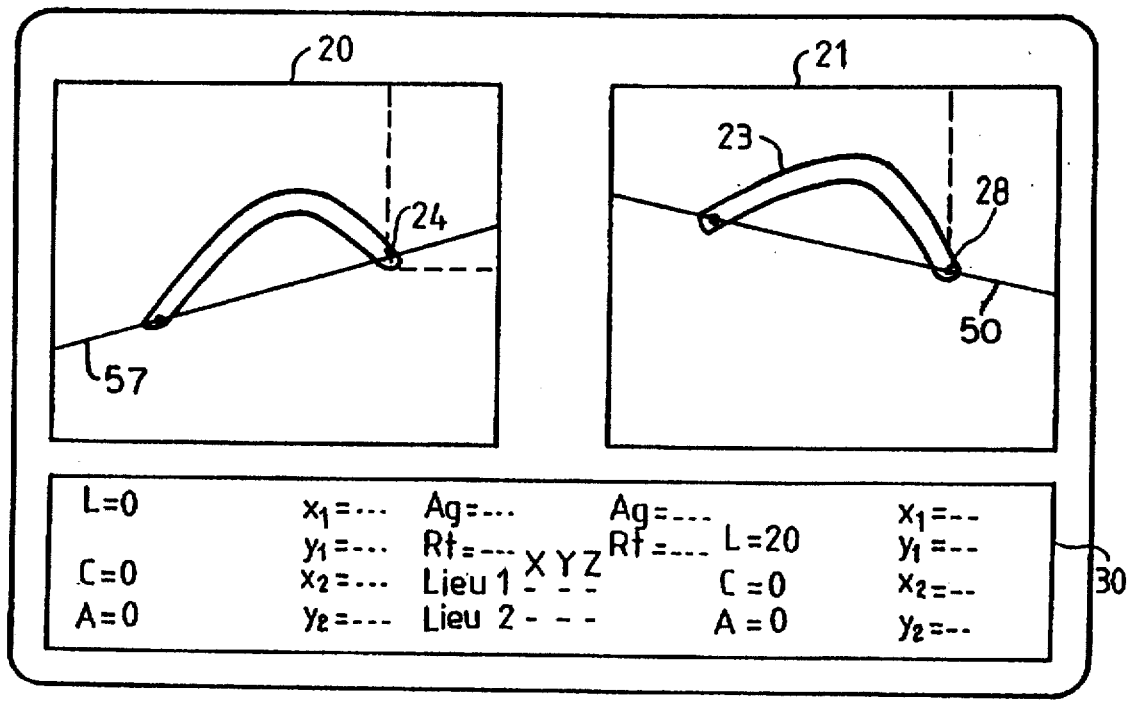

5,699,446

METHOD FOR THE ACQUISITION OF IMAGES OF A BODY BY THE ROTATIONAL POSITIONING OF A RADIOLOGY DEVICE, NOTABLY AN ANGIOGRAPHY DEVICE

BACKGROUND OF THE INVENTION

1. Field of the Invention

An object of the present invention is a method for the acquisition of images of a body by the rotational positioning of a radiology device. It can be used chiefly in medicine, notably in angiography. The method consists in acquiring images of a body by making a radiology device rotate about this body. An image is acquired for each of the different angles of incidence. The images obtained in this way can subsequently be processed, notably by algorithms of the type used in tomodensitometers, to carry out a reconstruction, in volume, of a system of arteries and veins. The aim of the invention is to enable the acquisition device to be secured about a particular reclining object that is contained in this body and that has to be imaged as precisely as possible.

2. Description of the Prior Art

According to common practice, an angiographic examination consists first of all in taking a number of views systematically along angles of incidence (front, side, oblique etc.) that are determined according to the anatomical region concerned and the operator's experience. Then, depending on what is seen along these first angles of incidence (the presence or suspicion of a lesion, the type and morphology of a lesion, etc.), other acquisitions are made along new angles of incidence that enable closer observation of the region of interest. Measurements are sometimes made along these new angles of incidence in order to quantify the lesion observed (in terms of narrowing or growth on a vessel for example).

The choice of these angles of incidence in space sometimes raises problems, notably because of the complexity of the scene observed and because of possible superimposition on other vessels. Furthermore, owing to the conical shape of the X-ray beam, the measurements made are accurate only if the local direction of the vessel is parallel to the plane of the detector. This is difficult to achieve in practice. The quality of the display and of the quantification of the lesions therefore depends greatly on the choice of the angles of incidence of acquisition.

The usefulness of securing an axis formed by the focal spot and the detector of the acquisition machine substantially perpendicular to an elongated object located in the body under examination is known from a lecture by Joseph SITOMER et al, "Computer Image-Guided Gantry Positioning With Respect To Patient Coronary Anatomy For Optimization Of Quantitative Coronary Arteriography", September 1987, Louvain, Belgium. The body being examined is, for example, a patient's body, the patient himself being positioned in a reclining direction (head-to-foot) while, in this body, a reclining object such as a particular coronary artery for example may have any orientation. If the image sought is an image of a coronary artery or else that of a blood vessel in the brain, then it is recommended that the machine be positioned so that it rotates about an axis that is substantially colinear with the reclining direction of the object.

The possibility of positioning the plane of a detector of the apparatus in a position parallel to the main axis of a vessel would enable the vessel to be displayed with the utmost efficiency.

Unlike standard systems, angiographic systems with three rotational axes offer the possibility of carrying out dynamic acquisitions in rotation about any axis in space by a very simple mechanical motion: by using the rotation about one of the three axes. However, this potentiality remains unused because its implementation cannot be achieved in clinical practice, there being no a priori knowledge of the 3D orientation of the vessels. An object of the invention is to propose a tool as an aid in the positioning of the system in order to determine the useful angles of incidence. The invention relates more specifically to the positioning of the detector in parallel to the reclining object, even if several images at different angles of incidence in rotation are neither required nor taken.

The first general principle of the invention consists of the use of two reference images acquired at two different angles of incidence in order to automatically determine the 3D orientation of the vessel of interest. Then, a triaxial machine is used to determine the angular positions of the first two axes in order to position the third axis in a position parallel to the vessel. The rotation about this third axis is then used freely to carry out the acquisitions. This principle meets the constraints linked to the examination. These constraints are that there are neither geometrical calibration procedures nor any correction of distortions using phantoms that would make the examination cumbersome or even impossible to carry out under routine clinical conditions. The only information on the acquisition geometry consists of the geometrical parameters on the position of the system such as they are given by design or by sensors of the position of the system. Owing to their calibration by design, these position sensors give information elements that are precise enough to determine the conditions of the examination.

Furthermore, for a triaxial machine, the invention recommends a particularly simple form of setting the machine once the main direction of the reclining object has been detected.

SUMMARY OF THE INVENTION

An object of the invention, therefore, is a method for the acquisition of images of a body by the positioning of an acquisition device, in rotation about an axis that is substantially colinear with an elongated object of this body, this device comprising an X-ray tube linked to a plane detector, the plane of the detector being substantially perpendicular to a direction of aim that passes approximately through a focal spot of the tube and through a midpoint of this plane of the detector, this tube and this detector being liable to occupy any positions in rotation in the space about the body, wherein said method comprises the following steps:

the spatial positions of the coordinates of focal spot of the tube and of the detector are acquired, i.e., the coordinates of the focal spot are acquired;

for two positions of the device, two images of the body are acquired, these images including images of the reclining body;

on a first image and in space, a first point representing a first characteristic locus of the direction of the reclining object is designated and localized;

the spatial coordinates of a projection straight line going through this first point and the focal spot of the tube are computed;

an epipolar straight line, which is the image of this projection straight line, is represented in the second image;

in this second image and in space, on the epipolar straight line, a point homologous to the first point is designated and localized;

the position in space of the first characteristic locus is deduced from the localizations of the points in the two images;

these operations are reiterated for a second characteristic locus;

the direction of the reclining object is deduced therefrom;

and the image or images in rotation are then acquired by making the device occupy one or more rotational positions about an axis that is substantially colinear with that of the reclining object.

As a variant, instead of localizing points of images of a segment of interest, image lines of this segment are identified. It will be shown that this variant is even faster (and more ergonomical) without any significant drawbacks as regards the result obtained.

BRIEF DESCRIPTION OF THE DRAWINGS

The invention will be understood more clearly from the following description and from the figures that accompany it. These figures are given purely by way of an indication and in no way restrict the scope of the invention.

Of these figures:

FIG. 1 shows a triaxial machine that can be used by preference to implement the method of the invention;

FIG. 2 shows a schematic view of the steps for computing the values for setting the machine according to a first variant of the invention;

FIG. 3 represents a help screen showing the information elements needed to implement the invention in this first variant;

FIGS. 4 and 5 show same views as in FIGS. 2 and 3, but with a different preferred approach;

MORE DETAILED DESCRIPTION

Figure 6A:
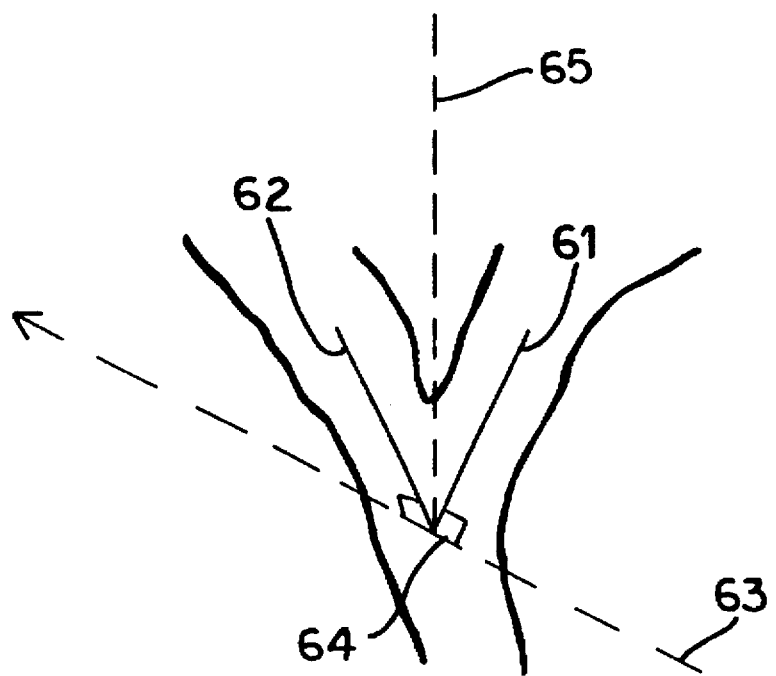
FIGS. 6a and 6b indicate choices of preferred orientations of the radiology device.

FIG. 1 shows an image acquisition device to implement the method of the invention. This device has an L-shaped pedestal or leg 1. This leg 1 is provided with a substantially horizontal base 2 and a substantially vertical beam or mast 3. The beam is fixed to an end 4 of the base. At another end 5, the base is provided with a vertical rotational axis parallel to the beam 3. In one example, the leg is capable of rotating by plus or minus 95° in relation to a reference orientation. The instrument also has a support arm 6. The support arm 6 is fixed by a first end, rotationally, to the top 7 of the beam 3. The rotational axis 8 of the support arm 6 is horizontal. Its amplitude of rotation, in one example, is plus or minus 117° about a mean position. The support arm 6 has a bayonet shape in one example. A circular C-arm 9 is held in a rotational sliding position by another end 10 of the support arm 6. The C-arm 9 maintains an X-ray tube 11 and an image detector 12 in diametrically facing positions. The detector 12 has a plane detection surface. A direction of aim is determined by a straight line linking a focal spot of the tube 11 to a midpoint of the plane of the detector 12. The C-arm 9 may rotate in a sliding motion in the end 10 about an axis 13. In one example, the C-arm 9 may rotate from plus 45° to minus 50° about a mean resting position.

The three rotational axes of the leg 1, the support arm 6 and the C-arm 9 are isocentric. They meet at a point 14 in space. In the mean position, these three axes are perpendicular to one another. Given the bayonet shape of the support arm 6 as presented, the tube 11 and the detector 12 are mounted laterally on diametrically opposite ends of the C-arm 9.

A patient is to lie on a patient's examination table 15 whose longitudinal orientation is designed to be aligned with the axis 8 when the orientation of the leg 1 is at rest: 0°.

There is a known way, theoretically, with a triaxial machine such as this, of orienting it so that the axis 13 or the axis 8 is colinear with a given direction. We shall see how, with the invention, firstly it is easy to find this given direction and, secondly, once it has been found it is easy to meet this direction.

FIG. 2 shows a body 16 in the position that it would occupy in the device of FIG. 1 and, inside this body, a reclining object whose direction in space needs to be known.

In the invention, the positions in space of the leg 1, the support arm 6, the C-arm 9, the tube 11 and the detector 12 are localized. The positions in space of the leg 1, the support arm 6 and the C-arm 9 may be known by the measurement, at each time, of only one value: the angle of orientation of these elements with respect to a reference. It is enough simply to place angular positional sensors on the three axes concerned to carry out measurements and deduce the corresponding positions therefrom. As regards the positions of the tube 11 and of the plane of the detector 12, the knowledge, from the design of the device, of the position of each of these two parts at the diametrically opposite ends of the C-arm 9 when the machine is in a mean position is essentially enough for the subsequent deducing therefrom of their positions throughout space in relation to a general reference. In practice, the focal spot of the X-ray tube 11 will be fixed with respect to one end of the C-arm 9 while, along the direction of aim, the plane of the detector 12 could move in a direction parallel to itself to prompt a zoom effect or even to be capable of rotating on itself so as to give the practitioner images in a more ergonomical way. For the time being, it shall be assumed that the orientation and the position of the detector 12 are fixed. In one example, the distance between the focal spot and the detector 12 is of the order of 70 cm. The focal spot and the center of the detector 12 are not necessarily equidistant from the isocenter 14. In the example, the distance between the detector 12 and the isocenter 14 is equal to about 30 cm.

For two positions 18 and 19 respectively of the focal spot of the X-ray tube 11 and, correspondingly, positions 20 and 21 of the plane of the detector 12, an image of the body 16 is acquired. In acquiring these two images, every attempt is made to center these images 22 and 23 respectively of a reclining or elongated object 17 of the body 16 so that they occupy substantially the center of the planes of the detectors. This is not an indispensable condition but gives the operation greater precision and makes it easier to perform In a first image, referenced 20 herein for purposes of simplification, a first point 24 representing a first locus 25 in the object 17 is designated. The first locus 25 is a first characteristic locus of the direction of the reclining object. It is, for example, one of its ends. Since the positions of the focal spot 18 and of the plane 20 of the detector 12 are known in space, it is possible to know the position, in space, of a straight line 26, called a projection line, passing through this focal spot and through the image 24 of the locus 25. Since the positions in space of the focal spot 19 and, correspondingly, of the plane 21 of the detector are also known, it is possible to compute the projected trace 27, called the epipolar line, in the second image 21 of the projection line 26. In the invention, the epipolar line 27 of this line 26 is displayed on a screen which shows each of the two images 20 and 21 side by side.

It is indeed possible to compute the coordinates, in space, of a plane containing the loci 18 and 19 of the focal spots, and the point 24 whose position in space is also known. It is then possible to compute the coordinates, in space, of the line 27 of intersection, of this plane, with that of the detector 12 in the position 19-21. The position of this line 27 is then computed in a reference related to the plane of the detector 12. These computations are within the scope of a final-year college student.

It is then possible, in the image 21, to designate or mark a point 28 located at the intersection of the trace 23 of the object 17 and the trace 27 of the straight line 26. Once the point 28 is thus marked, it can also be localized in the image 21 so that its coordinates can be known, firstly in this image 21 and, secondly, in space since the position of the image 21 is itself known. These operations of localization and designating are carried out with a computer system using a mouse or similar device, and a graphic screen management software. The result thereof is that the positions, in space, of the points 18, 19 and 24, 28 are now known. Now, the two straight lines 18-24 and 19-28 intersect at a point which is the locus 25. The position is space of the locus 25 is therefore now known by computation.

The same operation is reiterated for another locus 29 that is a characteristic locus of the object 17.

At the end of this operation, for each image, values L, C, A of rotational angles respectively of the leg 1, the support arm 6 and the C-arm 9, automatically computed by means of computations mentioned further below, appear in a box 30 of a screen of a computer device. Also displayed are coordinates, in the plane of the detector (having two dimensions x, y), of the first and second points representing the first and second characteristic loci x1, y1, x2, y2. Once these elements are known, a computing automation displays the values X, Y, Z of each of the characteristic loci 25 and 29. Polar coordinates rather than Cartesian coordinates could be chosen to display these loci.

In one improvement, the positions of the detector images 20 and 21 with respect to the focal spot of the X-ray tube 11 may be brought closer to each other in varying degrees to produce an effect of magnification. In this case, firstly information elements Ag pertaining to this magnification will be measured and displayed in the box 30. Secondly, the computations for changing the localized point will be modified as a function of this magnification.

After this, it might be sought to present the images 20 and 21 accurately on the screen of FIG. 3. For example, it may be desired that the top of the body should always correspond to the top of the image. Since this cannot be done systematically, if the leg 1 has been rotated then the detector 12 will be rotated, in the opposite direction about the axis of aim. The angle Rt of this rotation is measured for each image. The measurements of magnification and of image rotation angle are used to modify the computations of changes of axis which can be used to determine the positions in space of the loci 25 and 29 respectively.

If ΘL and ΘC are respectively taken to designate the rotational positions of the leg 1 and of the support arm 6 in the desired position, then these angles can be computed on the basis of the Cartesian coordinates of the two characteristic loci 25 and 29. After computation, these angles have the following values:

$$\Theta L = \text{Arctan} - (X2-X1)/(Y2-Y1)$$

$$\Theta C = \text{Arctan}(Z2-Z1)/\sqrt{((X2-X1)^2 + (Y2-Y1)^2)}$$

The apparatus of FIG. 1 can then be adjusted by imposing the values thus computed on the angles ΘL and ΘC.

Whatever the method used to obtain the direction of the reclining object 17, in the case of a triaxial machine, the leg 1 will preferably be adjusted so that the direction of the rotational axis 8 of the support arm 6 is perpendicular to a vertical plane passing through the object 17. Once this position is reached, the support arm 6 will be rotated about the axis 8 so that the plane of the C-arm 9 is perpendicular to the reclining orientation of the object. The images in rotation are then acquired by making the C-arm 9 slide about its axis 13. The above two formulae express this procedure for an automatic setting procedure: servo-controlled motors impose the rotations ΘL and ΘC on the leg and on the support arm.

To acquire even better images, it is preferable to make the isocenter 14 of the apparatus coincide with the midpoint of the segment 25-29 between the two characteristic loci. To this end, the coordinates of this midpoint 31 are computed with the coordinates of these points, and the coordinates of this midpoint are compared with the coordinates in space of the isocenter. Subtraction is used to deduce triaxial translation values to be imposed on the examination table 15 so that the patient's body can be accurately positioned.

When the two images are acquired, rather than choosing orientations forming an angle, with each other, of 90° which in principle is the best value for this angle, the orientations chosen for the device are such that the axes of aim of the images 20 and 21 form an angle of about 20° with each other. Indeed, the greater the angle, and the closer it is to 90°, the greater is the precision with which the loci 25 and 29 are computed. However, in this case, it will be difficult to recognize homologous points of one and the same characteristic locus in each image. Hence, instead of choosing high precision, low precision will be chosen (with a low divergence: 20° between the two directions of aim), and points that are then easily recognizable are chosen in the images. Experience shows that the precision is sufficient given the experimental conditions.

A description has been given, in the particular case of a triaxial machine, of a final rotation of the C-arm. However, a rotation about any horizontal axis may be obtained in other ways, notably by the rotation of the support arm 6 on itself. In particular, when the reclining object 17 is horizontal, it is possible to use a final rotation that is a rotation about the axis 8. In this case, the value at which the angle of the leg 1 is set must be offset by 90° with respect to the measurement described here above.

The triaxial machine described here above does not necessitate a comparison of the rotation about two axes. However, it is possible to envisage the combination of one rotation with another one, in a special machine, to obtain a rotation whose axis would be colinear with the reclining object.

FIGS. 4 and 5 show the same elements as those shown until now except that, instead of projection lines and epipolar lines, the figures, according to the invention, will show projection planes. For example (FIG. 4) whereas, in its positions 18 and 19 respectively, the machine had taken the shots or images 20 and 21, a straight line 50 that goes through the two ends 51 and 52 of a segment 53 to be identified in an image will be made to shift and will be placed on a first shot and then on another, for example first of all on the shot or image 21. This straight line can be made to move by any means, either by marking or designating two points of this straight line (which are not necessarily points 51 and 52 corresponding to ends of the object 17) and by tracing it or by means of a software drawing tool of the kind widely available in the market. Once this straight line 50 has been plotted, it is known that, with the locus 19 of the focal spot, it defines a plane 54 which shall be called a projection plane. The plane 54 is called a projection plane because this plane 54 bears a segment 55 going through the loci 25 and 29. At this stage of construction, there is no knowledge, however, of where the segment 55 is located in the plane 54. All that is known is that it is in this plane. Ergonomically, it is easier to draw a straight line than it is to mark two points. The second method is simpler. It does not require the display of the two images simultaneously on the same screen nor the defining of precise corresponding points in the two images. Even less does it require going back and forth between the two images: one image is processed and then another one, and that is the end of the operation.

The same operation is repeated to define another plane 56, also called a projection plane for the same reasons, by means of the image 20. This plane 56 is defined by the position of the focal spot at 18 and by a straight line 57 which goes through the images 58 and 59 of the loci, 29 and 25 respectively, of the ends of the segment 55 of interest.

FIG. 5 shows the straight lines 50 and 57 that are obtained. It has been seen that, from these straight lines, it is possible to define the planes 55 and 56. Now, these projection planes intersect each other along a straight line that contains the segment 55. At this stage, the position of the segment 55 on this straight line is not known but its exact direction in space is already known, at least with respect to the radiology machine. Indeed the positions of the planes 54 and 56 can be localized with respect to a given position of the radiology machine. It is of course easy to localize their intersection in space in relation to one and the same reference point related to the radiology machine. There is therefore no need even to localize the segment 55 in an absolute referential system with respect to which, for example, the patient would be localized.

However, the position of the segment 55 on the straight line that bears it is not known. Initially, it will be assumed that this lack of precision is not troublesome as the operator who has stopped the radiology machine in order to make it assume the positions 18 and 19 will have been skilled enough to choose a position such that the useful image will always be approximately centered. It is therefore possible to accept this lack of precision in order to carry out the definitive positioning of the radiology machine about the axis passing through the segment 55 and launch the rotational acquisition. To this end, the above-mentioned rotations are carried out by assuming that the midpoint of the useful segment 55 corresponds to the isocenter of the machine in the position that it occupies.

However, it can also be seen that the planes 55 and 56 are not infinite. They are bordered by straight lines that go through the focal spot and, at the same time, through the edges of the images 20 and 21. These planes, whose definition is thus limited, can be used to define a limited segment 55. The limited segment 55 is shown with a heavy line in the figure. This limited segment 55 has the advantage of including the segment 25-29 of interest. The lack of precision with which the limited segment 55 is determined is itself limited, so that it becomes possible to define a center 60 of this limited segment 55 and make the settings of the radiology machine, as seen here above, by using this approximate center 60.

This indeterminacy, which results from higher speed and greater simplicity of use of the method of the invention, may furthermore be completely eliminated by the plotting, in the second image, of the epipolar straight lines associated respectively with the points 51 and 52. This method is then more robust because it uses only the directions of the objects.

When elements other than segments have to be displayed, for example when it is necessary to display a bifurcation between vessels as can be seen in FIG. 6a, it is possible, with two segments 61 and 62 each pertaining to one direction, to determine a plane of bifurcation that contains both segments as well as a normal 63 to this plane at their point of intersection 64. It is then possible to define a radiological axis of the radiology machine, centered on this point of intersection 64, that is oriented as this normal 63. This radiological axis could also be oriented as the bisector of the angle formed by the two directions of these two segments. In this case, an intersection is furthermore chosen as the midpoint of a segment of interest.

Figure 6B:
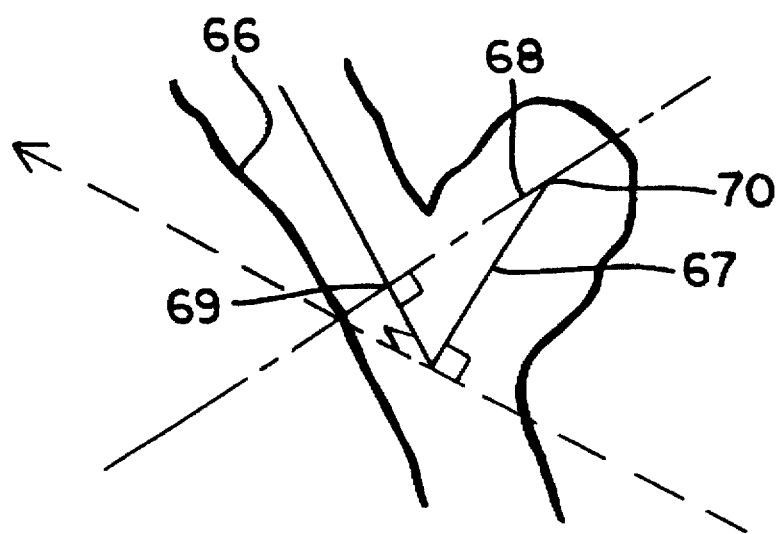

It may also be desired to show an aneurysm as can be seen in FIG. 6b. Several possible approaches can be used to find an axis perpendicular to an aneurysm in such a way as to reveal its neck as clearly as possible. It is possible to make a rotational acquisition about the axis 66 of the vessel (or the axis 67 of the aneurysm). This could be done for example, as seen here above, first of all by determining this axis 66. Then it is possible to choose visually, as another second image, an image where the plane defined by the axis of the vessel and the plane of the aneurysm are parallel to the image plane. The method seen here above is then used to determine a second axis (the axis 67 or the axis 66) and the definitive acquisition, as referred to here above, is done by choosing, with these two axes, an orientation that is normal to the plane or is a bisector.

A second approach consists in carrying out an acquisition of the vessel along its length. This approach makes it possible to see how the aneurysm is located in the plane perpendicular to the vessel. Then, a rotational axis is defined in this perpendicular plane. This is shown in FIG. 6b. A swifter method consists in computing this perpendicular directly in the plane defined by the axes 67 and 66 of the aneurysm and of the vessel. This plane being known, it is possible to bring about the movement therein (with a mouse or a trackball) of a straight line 68 that is perpendicular, by design, at 69 to the axis 66 (or 67). A particular position of this straight line 68 is chosen, at the place where it furthermore goes through a midpoint 70 of the aneurysm. Then a rotational segment borne by this straight line 68 is chosen by centering the operation, for example, on the midpoint of the segment 69–70.

What is claimed is:

1. A method for the acquisition of images of a body by the positioning of an acquisition device, in rotation about an axis that is substantially collinear with a direction of extension of an elongated object of the body, the device comprising an X-ray tube linked to a plane detector, the plane of the detector being substantially perpendicular to a direction of aim that passes approximately through a focal spot of the tube and through a midpoint of the plane of the detector, the tube and the detector being movable relative to one another and to the body so as to be capable of occupying any positions in rotation in the space about the body, wherein said method comprises the following steps:

(A) ascertaining coordinates, relative to a frame of reference, of positions in space of the focal spot of the tube and of the detector;

(B) operating the device, for two different positions of the device, so as to acquire first and second images of the body, said images including images of the elongated object;

(C) designating, on the first image, a first point representing a first characteristic locus of the direction of extension of the elongated object, and then computing spatial coordinates of said first point relative to the frame of reference;

(D) computing, relative to the frame of reference, spatial coordinates of a projection straight line going through the first point on the first image and through the focal spot of the tube;

(E) displaying, in the second image, an epipolar straight line which is the image of the projection straight line;

(F) designating, in the second image, and on the epipolar straight line, a point homologous to the first point, and then computing spatial coordinates of said homologous point relative to the frame of reference;

(G) deducing, from the computations of the spatial coordinates of the first and homologous points of the first and second images, coordinates, relative to the frame of reference, of the position in space of the first characteristic locus;

reiterating operations (C) through (G) for only one second characteristic locus of the direction of extension of the elongated object;

deducing the direction of extension of the elongated object from the deduced positions in space of the first and second characteristic loci;

and then making the device occupy one or more rotational positions about an axis that is substantially collinear with that of the elongated object and acquiring an image of the elongated object for each said rotational position of the device.

2. A method for the acquisition of images by rotation of an acquisition device about an axis that is substantially collinear with a direction of extension of an elongated object of the body, the device comprising:

a generally L-shaped leg including 1) a substantially horizontal base and 2) a mast which has a lower end that is fixed to one end of the base and which extends substantially vertically upwardly from the base, said leg being rotatable about a substantially vertical axis which goes through another end of the base and which is parallel to the mast, a horizontal support arm which has an end that is mounted to the top of the mast and which is capable of rotating about a horizontal axis with respect to the mast, and a C-arm, borne, in a sliding motion and in rotation, by another end of the support arm, the C-arm supporting, in diametrically opposite positions, an X-ray tube and a plane detector, the plane of the detector being substantially perpendicular to a direction of aim that goes approximately through 1) a focal spot of the tube, 2) a rotational axis of the C-arm, and 3) a midpoint of the plane of the detector, the rotations of the leg, the support arm and the C-arm being isocentrical and occurring about the body, wherein said method comprises the following steps:
deducing the direction of extension of the elongated object;
rotating the leg, and hence the support arm and the C-arm, about the substantially vertical axis so that the direction of the rotational axis of the support arm is perpendicular to a vertical plane going through the object;
rotating the support arm with respect to the leg so that the plane of the C-arm is perpendicular to an elongated orientation of the object;
and then making the C-arm slide rotationally about its axis between at least two positions thereof and acquiring an image of the elongated object at each of said positions.

3. A method according to claim 2 wherein, to deduce the direction of extension of the elongated object:

(A) spatial coordinates of the positions of the leg, the support arm, the C-arm, the tube and the detector are ascertained with respect to a frame of reference;

(B) first and second images of the body are acquired by the device for two different positions of the device relative to the body;

(C) on the first image, a first point representing a first characteristic locus of the direction of extension of the elongated object is designated and spatial coordinates of said first point with respect to the frame of reference are then computed;

(D) spatial coordinates of a projection straight line going through the first point and the focal spot of the tube are computed, said spatial coordinates being computed with respect to the frame of reference;

(E) an epipolar straight line, which is the image of the projection straight line, is displayed in the second image;

(F) in the second image, and on the image of the epipolar straight line, a point homologous to the first point is designated, and spatial coordinates of said homologous point relative to the frame of reference are computed;

(G) coordinates, relative to the frame of reference, of the position in space of the first characteristic locus is deduced from the computations of the spatial coordinates of said first and homologous points in the first and second images;

the operations (C) through (G) are reiterated for a second characteristic locus of the direction of extension of the elongated object;

and the direction of extension of the elongated object is deduced from the first and second characteristic loci.

4. A method for the acquisition of images of a body by the positioning of an acquisition device in rotation about an axis that is substantially collinear with an elongated object of the body, the device comprising an X-ray tube linked to a plane detector, the plane of the detector being substantially perpendicular to a direction of aim that passes approximately through a focal spot of the tube and through a midpoint of the plane of the detector, the tube and the detector being movable relative to one another and to the body so as to be capable of occupying any positions in rotation in the space about the body, wherein said method comprises the following steps:
ascertaining spatial coordinates of positions of the focal spot of the tube and of the detector relative to a frame of reference;
operating the device, for two different positions of the device, so as to acquire first and second images of the body, the first and second images including traces of the elongated object;
displaying, on the first image, a first straight line representing a characteristic segment of the direction of extension of the elongated object and then computing spatial coordinates of said first straight line relative to the frame of reference;
computing spatial coordinates relative to the frame of reference of a first projection plane going through the first straight line and the focal spot of the tube;
displaying, in the second image, a second straight line which also represents the characteristic segment of the direction of extension of the elongated object, and then computing spatial coordinates of said second straight line relative to the frame of reference;

computing the coordinates in space relative to the frame of reference of a second projection plane going through the second straight line and the focal spot of the tube;

deducing the direction of the characteristic segment and the direction of extension of the elongated object from the computations of the coordinates of the first and second projecting planes;

and then making the device occupy one or more rotational positions about an axis that is substantially collinear with that of the elongated object and acquiring an image of the elongated object for each said rotational position of the device.

5. A method according to claim 4, further comprising the following steps:

computing the coordinates, relative to the frame of reference, of the position of the focal spot of the tube in relation to the plane of the detector, and identifying the direction of extension of the elongated object in relation to the plane of the detector.

6. A method according to claim 4, further comprising the following steps:

computing the coordinates relative to the frame of reference, of the position of the focal spot of the tube and the plane of the detector in relation to a fixed reference in space, and identifying the direction of extension of the elongated object in relation to said fixed reference in space.

7. A method according to claim 1, the device comprising:

a generally L-shaped leg including 1) a substantially horizontal base, and 2) a mast which has a lower end that is fixed to one end of the base and which extends substantially vertically upwardly from the base, the rotational axis of said device going through the other end of the base and being parallel to the mast, a horizontal support arm which has a first end that is mounted to the top of the mast and which is capable of rotating about a horizontal axis with respect to the mast, and a C-arm, borne, in a sliding motion and in rotation, by a second end of the support arm, the C-arm supporting, in diametrically opposite positions, an X-ray tube and a flat detector, the plane of the detector being substantially perpendicular to a direction of aim that 1) goes approximately through a focal spot of the tube and a midpoint of the plane of the detector, and that 2) intersects a rotational axis of the C-arm, the rotations of the leg, the support arm and the C-arm being isocentrical and performed about the body, wherein said method further comprises the following steps:

ascertaining spatial coordinates of the positions of the leg, the support arm, the C-arm, the tube and the detector relative to the frame of reference;

and then acquiring the images in rotation by making the C-arm slide rotationally about an axis that is substantially collinear with that of the elongated object.

8. A method according to claim 7, wherein, in order to acquire the images in rotation:

the leg is rotated about the rotational axis of the device so that the direction of the rotational axis of the support arm is perpendicular to a vertical plane going through the elongated object;

the support arm is rotated with respect to the mast so that a plane of the C-arm is perpendicular to the elongated orientation of the object;

and then the C-arm is made to slide with respect to the support arm.

9. A method according to claim 4, wherein the elongated object extends in a first elongated direction and a second elongated direction that are convergent at a point, and wherein there is deduced, from the two directions of extension of the elongated object, a direction of extension that is perpendicular, at this point of convergence, to the plane formed by these two directions of extension, and one or two images in rotation are then acquired while making the device occupy one or more rotational positions about an axis that is substantially collinear with that of the perpendicular direction of extension.

10. A method according to claim 4, wherein the elongated object extends in a first elongated direction and a second elongated direction that are convergent at a point, and wherein there is deduced, from the two directions of extension of the object, the coordinates of a direction of exploration that is a bisector of these two directions and is contained in a plane formed by these two directions of extension, and one or two images in rotation are then acquired while making the device occupy one or more rotational positions about an axis that is substantially collinear with that of the direction of exploration.

11. A method according to claim 1, wherein the two images of the object are taken while this object occupies the center of the image.

12. A method according to claim 1, wherein the two images of the object are taken while the direction of aim of the detector takes orientations that diverge from each other by 20°.

13. A method according to claim 1, further comprising displaying the two images on a screen of a computer system with, for each image:

values representing the orientations of the leg, the support arm, the tube, and the detector relative to the frame of reference;

values representing coordinates, relative to the frame of reference, of positions in the images of the points and of the first and second characteristic loci.

14. A method according to claim 1 wherein, before the images in rotation are acquired:

the body is shifted with respect to the device so that the midpoint of the characteristic loci is substantially merged with an isocenter.

15. A method according to claim 1 wherein, before the images in rotation are acquired:

the detector is rotated about its axis of aim to present the images differently.

* * * * *